United States Patent
Chan et al.

(12) 
(10) Patent No.: US 8,355,770 B2
(45) Date of Patent: Jan. 15, 2013

(54) CONDUCTIVE SILICONE MATERIAL FOR HUMAN SKIN ELECTRODE

(75) Inventors: Raymond Chan, Hong Kong (HK); Mun Hoong Leong, Hong Kong (HK); Li Li, Shenzhen (CN)

(73) Assignee: IDT Technology Limited, Hong Kong (CN)

( * ) Notice: Subject to any disclaimer, the term of this patent is extended or adjusted under 35 U.S.C. 154(b) by 459 days.

(21) Appl. No.: 12/729,206

(22) Filed: Mar. 22, 2010

(65) Prior Publication Data

US 2011/0230749 A1    Sep. 22, 2011

(51) Int. Cl.
*A61B 5/0408* (2006.01)
*H01B 1/04* (2006.01)

(52) U.S. Cl. ........ 600/395; 600/393; 600/382; 600/372; 29/825; 252/511

(58) Field of Classification Search ................... 600/393, 600/382, 390, 395; 252/502, 510, 511, 519.31, 252/521.3
See application file for complete search history.

(56) References Cited

U.S. PATENT DOCUMENTS

| | | | | | |
|---|---|---|---|---|---|
| 4,122,843 | A | * | 10/1978 | Zdrojkowski | 600/382 |
| 4,300,575 | A | * | 11/1981 | Wilson | 607/152 |
| 5,218,973 | A | * | 6/1993 | Weaver et al. | 607/152 |
| 5,336,442 | A | * | 8/1994 | Kuramochi | 252/511 |
| 6,775,566 | B2 | | 8/2004 | Nissila | |
| 7,324,841 | B2 | | 1/2008 | Reho et al. | |
| 2004/0073104 | A1 | * | 4/2004 | Brun del Re et al. | 600/372 |
| 2006/0094948 | A1 | * | 5/2006 | Gough et al. | 600/372 |
| 2006/0183990 | A1 | * | 8/2006 | Tolvanen | 600/386 |
| 2006/0211934 | A1 | | 9/2006 | Hassonjee et al. | |
| 2007/0285868 | A1 | | 12/2007 | Lindberg et al. | |

OTHER PUBLICATIONS

Princy et al. "Studies on Conductive Silicone Rubber Compounds," Journal of Applied Polymer Science 69; pp. 1043-1050 (1998).*
Calixto et al. "Development of Graphite-Polymer Composites as Electrode Materials," Materials Research 10(2); pp. 109-114 (2007).*
Ghosh & Chakrabarti "Conducting Carbon Black Filled EPDM Vulcanizates: Assessment of Dependence of Physical and Mechanical Properties and Conducting Character on Variation of Filler Loading," European Polymer Journal 36; pp. 1043-1054 (2000).*

* cited by examiner

*Primary Examiner* — Lee S Cohen
*Assistant Examiner* — Erin M Cardinal
(74) *Attorney, Agent, or Firm* — Eagle IP Limited; Jacqueline C. Lui

(57) ABSTRACT

A conductive silicone material for human skin electrode is disclosed. In one embodiment, the conductive silicone material comprises a mixture of silicone and carbon powder such that the mixture has a resistivity of 0.08 to 0.12 Ω·m and a Shore A hardness of 50 to 60. In an exemplary embodiment, the mixture comprises 60 to 80 weight percent silicone and 20 to 40 weight percent carbon powder. A sensor for detecting human biological signal using a conductive silicone electrode is also disclosed.

9 Claims, 2 Drawing Sheets

CONDUCTIVE SILICONE MATERIAL FOR HUMAN SKIN ELECTRODE

FIELD OF INVENTION

This invention relates to a conductive silicone material, in particular a conductive silicone material used for human skin electrodes.

BACKGROUND OF INVENTION

Human skin electrodes are used for detecting biological signals of a user, such as ECG signal. Conventional electrodes make use of adhesives or sewing for securing the electrode. There is a need for further improvement for more versatile securing of electrodes.

SUMMARY OF INVENTION

In the light of the foregoing background, it is an object of the present invention to provide an alternate material for human skin electrode.

Accordingly, the present invention, in one aspect, is a composition comprising a mixture of silicone and carbon powder, the composition having a resistivity of 0.08 to 0.12 $\Omega \cdot m$ and a Shore A hardness of 50 to 60.

In an exemplary embodiment of the present invention, the silicone is methyl vinyl silicone. In another embodiment, the carbon powder has a size in the order of 3-5 μm.

In another embodiment, the composition comprises about 60 to 80 weight percent silicone and about 20 to 40 weight percent carbon powder. In an exemplary embodiment, the composition comprises 70 weight percent silicone and 30 weight percent carbon powder.

According to another aspect of the present invention, a sensor for detecting human biological signal is disclosed. The sensor comprises a body substrate and at least two electrodes attached to the body substrate. The electrodes are made of a conductive silicone material comprising a mixture of silicone and carbon powder. The sensor also comprises an electronic unit electrically connected to the electrodes.

In an embodiment, the body substrate is made of a fabric material and the electrodes further comprise a non-conductive silicone attached to the conductive silicone. In an exemplary embodiment, the electrodes further comprise a fiber layer sandwiched between the conductive silicone and the non-conductive silicone.

In another embodiment, the body substrate is made of a non-conductive silicone.

In another aspect of the invention, a method of manufacturing a human skin electrode comprising a mixture of silicone and carbon powder is disclosed. The method comprises the steps of providing silicone, providing carbon powder, and mechanically mixing the silicone and the carbon powder together. The mixture is then formed into an electrode by injection molding.

There are many advantages to the present invention. For example, the conductive silicone is electrically conductive while still flexible enough to conform to human skin contour. The conductive silicone also possesses advantages such as stability in high and low temperatures, chemical resistance, moisture resistance, superior long term elastic properties and aging resistance. The moisture resistance property of the silicone composition according to the one implementation of the present invention assist in the retention of moisture to increase the conductivity between the electrode and the human skin on which it is attached. As a result, the amount of carbon material can be maintained at a percentage range of 20%-40%. This percentage is low enough for the silicone composition of the present invention to retain its flexibility.

DETAILED DESCRIPTION OF THE PREFERRED EMBODIMENTS

In the following description and in the claims, the term "carbon content" means the percentage of carbon by weight.

For a human skin electrode, there is an upper limit of input impedance before the signal detected is too weak and noisy to be accurate. This upper limit depends on the location and orientation of the electrode among other factors such as the circuitry used. For example, for a chest belt to be placed across a user's chest, typically the input impedance cannot exceed 700 ohms. In this invention, this is achieved by designing an alternate material for forming the electrode.

There are two main factors to consider when designing a material for human skin electrodes. First of all, the material must be electrically conductive to an extent such that the input impedance of the electrode meets the requirement even when the electrode is long and thin, which is usually the case for chest/arm belt electrode. The hardness or flexibility of the material is also important because it affects the ability of the electrode to follow the contour of the body, because the electrode is unable to detect any signal if the electrode is not in contact with human skin.

In the present invention, carbon powder is added to silicone to produce a conductive silicone material. In one embodiment, the silicone exists in a hydrated silicone form. In an exemplary embodiment, the silicone is methyl vinyl silicone (VMQ). An exemplary segment of the silicone polymer is shown below:

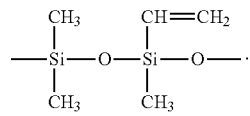

Figure 1:
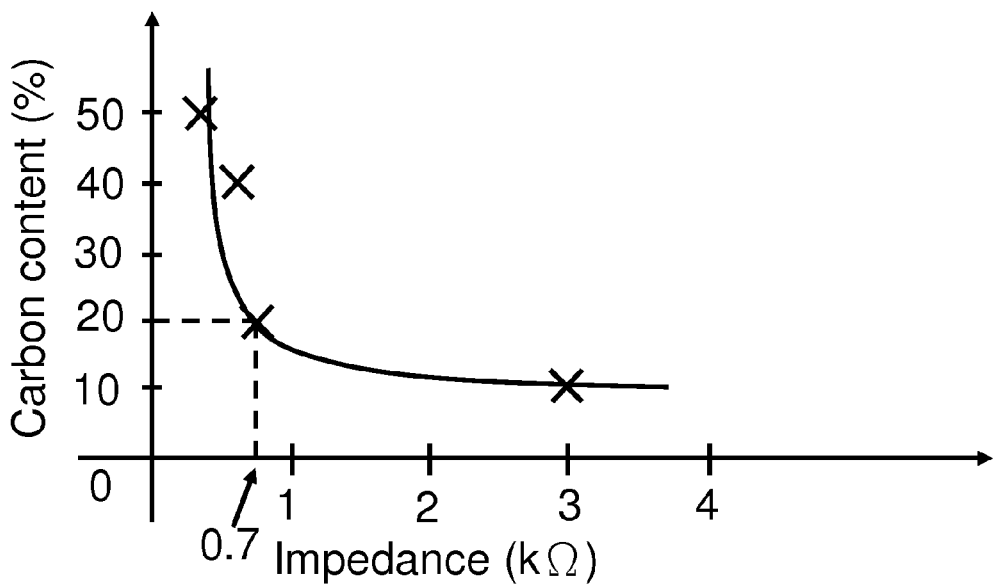
FIG. 1 is a graph showing the relationship between the carbon content in silicone and impedance of an electrode made from the silicone.

In one embodiment, the size of the carbon powder is in the order of a few micrometers. More carbon content increases the conductivity of the silicone, hence lower input impedance. For example, assuming the electrode size is 80 mm*25 mm*0.5 mm, at 10% carbon content the impedance is about 3000 ohm meaning that resistivity is 0.47 $\Omega \cdot m$, but at 50% carbon content the impedance drops to only about 200 ohm. The desired resistivity is 0.08 to 0.12 $\Omega \cdot m$, meaning the input impedance to be around 500 to 700 ohm. Table 1 below shows the relationship between carbon content and input impedance of the electrode. From table 1, it is shown that a 700 ohm impedance corresponds to a minimum carbon content of 20 weight percent and 500 ohm impedance corresponds to a carbon content of 40 weight percent. FIG. 1 is a fitting curve of table 1.

TABLE 1

Relationship between carbon content and impedance

| Carbon content (% by weight) | Impedance (ohm) |
|---|---|
| 10 | 3000 |
| 20 | 700 |
| 40 | 500 |
| 50 | 200 |

Figure 2:
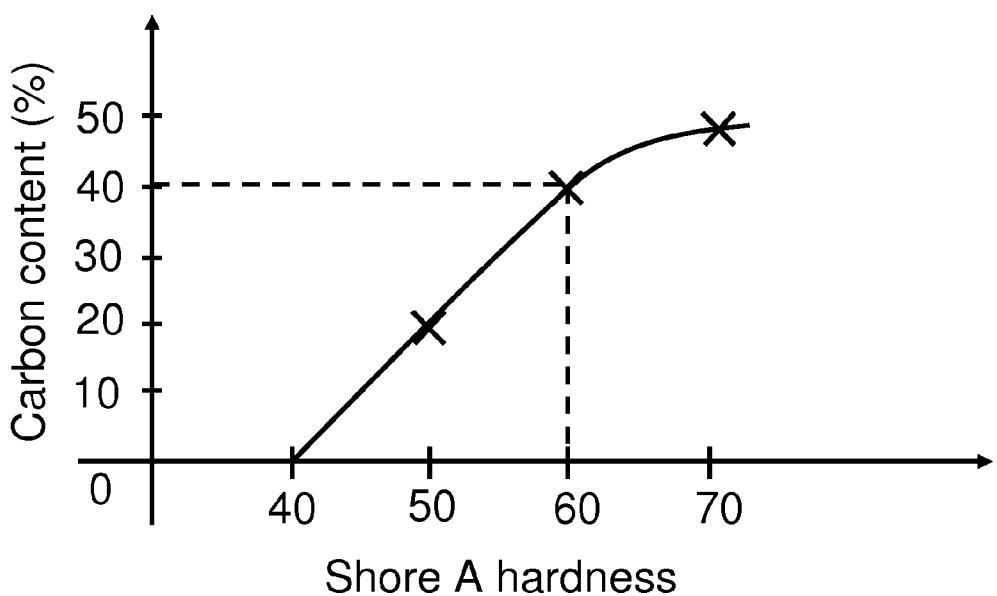
FIG. 2 is a graph showing the relationship between the carbon content in silicone and the Shore A hardness of the silicone.

However, while more carbon content will increase the conductivity of the silicone, it also increases the hardness of the silicone which is not desired. For example, at 20% carbon content the hardness is about 50, and will rise to 60 at about 40% carbon content and 70 at 50% carbon content. In accordance with the present invention, it has been found that at a Shore A hardness of more than 60, the silicone will not be able to easily conform to the human skin contour well any more, especially when used on people with a narrow chest such as children. FIG. 2 and table 2 shows the relationship between carbon content and hardness. From table 2, the maximum carbon content is found to be 40 percent by weight.

TABLE 2

Relationship between carbon content and Shore A hardness

| Carbon content (% by weight) | Shore A hardness |
|---|---|
| 0 | 40 |
| 20 | 50 |
| 40 | 60 |
| 50 | 70 |

Combining the two criteria above, the carbon content is found to be about 20 to 40 percent by weight, corresponding to a resistivity of 0.08-0.12 $\Omega \cdot m$. At this range of carbon content, the Shore A hardness is between 50 to 60. In an exemplary embodiment, the carbon content is 30% corresponding to a hardness of 55.

To manufacture the mixture as described above, the raw silicone rubber is mechanically mixed with the carbon powder at the desired weight percentages. In one embodiment, the silicone used is hydrated methyl vinyl silicone as disclosed above. In one embodiment, the carbon powder has a size in the order of 3-5 micrometers or 3000-6000 mesh. Then the electrode is formed using conventional techniques same as manufacturing standard non-conductive silicone. In an example, the electrode is formed by injection molding. Silicones other than MVQ can also be used as long as it can be mixed with the carbon powder and molded into shape.

In one embodiment, the conductive silicone is bonded to a non-conductive silicone on a non-contact surface, which means that the surface is not in contact with human skin when in use. The conductive silicone and non-conductive silicone are heated to temperature of 160 to 200 degrees Celsius and pressed under a pressure of 10 to 30 kg/cm for about 10 minutes to combine the two materials together. When bonded, the non-conductive silicone covers the non-contact surface of the conductive silicone, therefore that surface becomes non-conductive. In another embodiment, a layer of fiber is sandwiched between the conductive silicone and non-conductive silicone such that the electrode is more resistant to shear and tear. In the preferred embodiment, the fiber is a woven fabric such as cotton or nylon.

Figure 3:
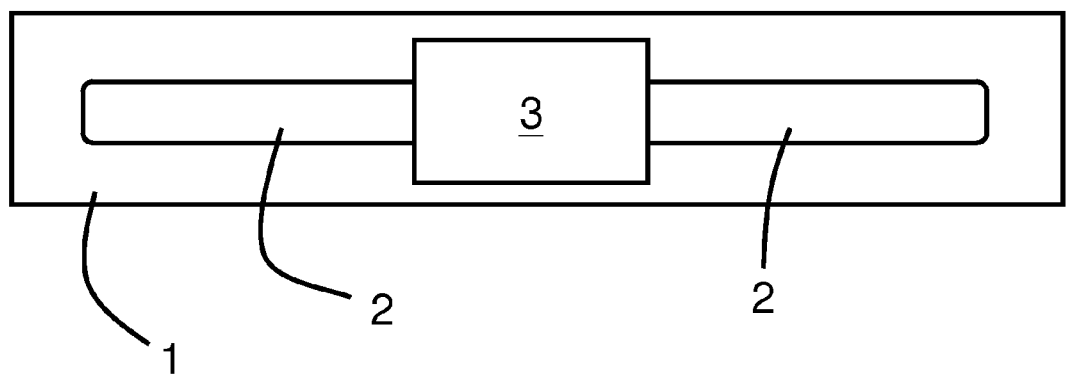
FIG. 3 is a top view of a chest belt having a conductive silicone electrode, according to an embodiment of the present invention.

FIG. 3 shows a first embodiment of a chest belt utilizing the electrode of the present invention. The chest belt comprises a body substrate 1, at least two electrodes 2 and an electronic unit 3 having processing circuitry therein. The electrode 2 is made up of silicone with carbon powder as described above. In a specific embodiment, the electrode 2 has a size of 80 mm*2.5 mm*0.5 mm and a carbon content of 30%. The body substrate 1 is made from non-conductive silicone. The body substrate 1 comprises a bonding area that is bonded to a non-contact surface of the electrode 2 using the method as described above, an attaching area that attaches to the electronic unit 3, and a surrounding area that surrounds the bonding area and the attaching area. The electronic unit 3 is electrically connected to the electrodes 2.

When the chest belt is in use, the user places the chest belt horizontally across his chest with a conductive contact surface of the electrodes 2 facing inwards and in contact with the user's skin. This orientation maximizes the potential difference between the two electrodes, but other orientations are also possible. The non-contact surface of the electrode 2 faces away from the user. In one embodiment, the chest belt is held in place by attaching the body substrate 1 to a belt at opposite ends of the body substrate 1, and the belt is wrapped around the user's body and tightened in order to hold the chest belt. The electrode 2 collects the potential difference when the heart beats and the signal is processed by the processing circuit in the electronic unit 3. The result is then displayed on the electronic unit 3 or on a remote device through a wireless connection between the electronic unit 3 and the remote device.

Figure 4:
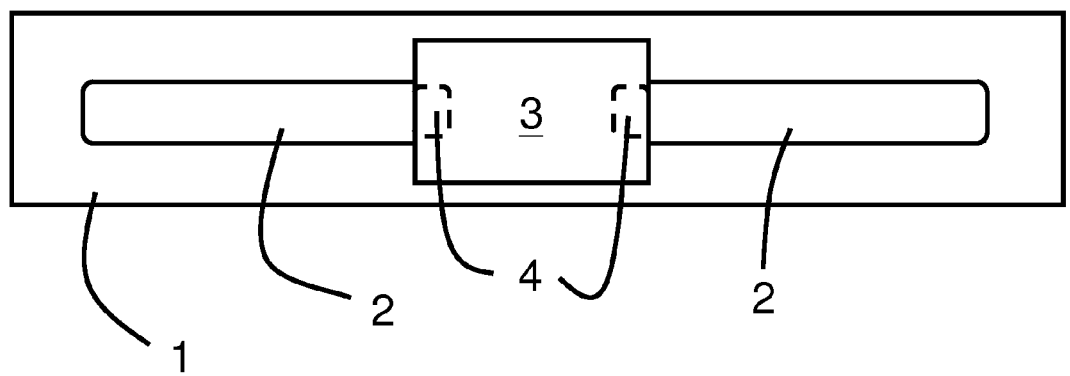
FIG. 4 is a top view of a chest belt having a conductive silicone electrode, according to another embodiment of the present invention.

In a second embodiment of the chest belt as shown in FIG. 4, the chest belt comprises a body substrate 1, at least two electrodes 2, an electronic unit 3 and a press stud 4 attached to the body substrate 1 for each electrode 2. The electronic unit 3 is reversibly attached and electrically connected to each electrode 2 at the same time through the electrically conductive press stud 4.

Figure 5:
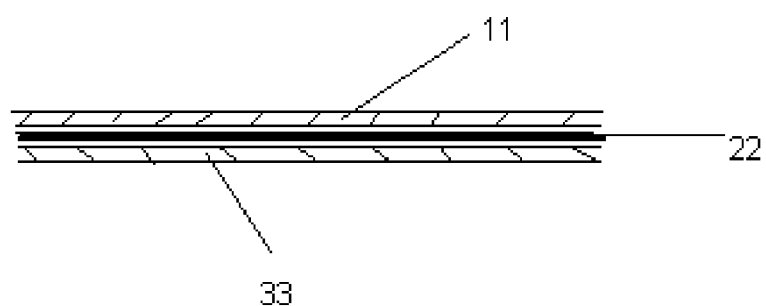
FIG. 5 is a cross sectional view of the electrode of the chest belt in FIG. 4.

In this embodiment, the body substrate 1 is made from a fabric material. As shown in FIG. 5, the electrode 2 is made up from a layer of conductive silicone 11, a layer of non-conductive silicone 33 and a layer of fiber 22 sandwiched between the above two layers. The layers are bonded together using the method described above, and then glued or sewed or otherwise attached to the body substrate 1.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, the conductive silicone can be coated with a non-conductive coating on the non-contact surface to insulate the conductive silicone from outside instead of bonding to a non-conductive silicone material.

The electronic unit 3 can be reversibly attached and electrically connected to the electrodes 2 through other mechanisms other than press stud 4. For example, the electronic unit 3 can be attached to the electrodes 2 through an electrically conductive clip. The electronic unit 3 can also be reversibly attached to the body substrate where at an attached position, the electronic unit 3 is electrically connected to the electrodes 2.

The above embodiments use a horizontally oriented chest belt for explaining the present invention. It is clear to one skilled in the art that other orientations are also possible, and different impedance requirements may be needed for other orientations.

Instead of carbon powder, other materials can also be added to silicone to produce the conductive silicone material, such as silver, copper or other metals. The human skin electrode can also include other materials other than silicone and carbon, such that the combined weight percentage of silicone and carbon does not need to be equal to 100 percent.

What is claimed is:

1. An article of manufacture comprising:
   a) a body substrate;
   b) at least two electrodes made of a conductive silicone material comprising a mixture of silicone and carbon powder, said at least two electrodes attached to said body substrate; and
   c) an electronic unit electrically connected to said at least two electrodes;
   wherein said body substrate is a fabric material and each of said at least two electrodes further comprises:
      i) a non-conductive silicone material between said conductive silicone material and said body substrate; and
      ii) a fiber layer between said conductive silicone material and said non-conductive silicone material.

2. The article of manufacture according to claim 1, wherein said silicone of said conductive silicone material is methyl vinyl silicone.

3. The article of manufacture according to claim 1, wherein said carbon powder of said conductive silicone material has a size of 3-5 micrometers.

4. The article of manufacture according to claim 1, wherein said conductive silicone material further comprises:
   a) about 60 to 80 weight percent of said silicone; and
   b) about 20 to 40 weight percent of said carbon.

5. The article of manufacture according to claim 1, wherein said conductive silicone material comprises:
   a) 70 weight percent of said silicone; and
   b) 30 percent of said carbon.

6. The article of manufacture according to claim 1, wherein said electrodes have an input impedance of about 500 to 700 ohm.

7. A method comprising steps of
   a) providing raw silicone rubber;
   b) providing carbon powder;
   c) mechanically mixing said raw silicone rubber and said carbon powder to form a mixture;
   d) forming a human skin electrode from said bounded mixture by injection molding;
   wherein said method further comprises a step of bonding said mixture to a non-conductive silicone material, said bonding step comprising steps of:
      i) sandwiching a fiber layer between said mixture and said nonconductive silicone material;
      ii) heating said mixture and said non-conductive silicone material to a temperature of 160 to 200 degrees Celsius;
      iii) pressing said mixture and said non-conductive silicone material together under a pressure of 10 to 30 kg/cm for at least 10 minutes.

8. The method according to claim 7, wherein said mixture comprises:
   a) about 60 to 80 weight percent of said raw silicone rubber; and
   b) about 20 to 40 weight percent of said carbon powder.

9. The method according to claim 7, wherein said mixture comprises:
   a) 70 weight percent of said raw silicone rubber; and
   b) 30 weight percent of said carbon powder.

* * * * *